United States Patent [19]

Ida et al.

[11] 4,298,449
[45] Nov. 3, 1981

[54] SAMPLE TRAY FEEDING APPARATUS

[75] Inventors: Hideaki Ida, Musashimurayama; Ryo Fujimori, Hachiouji, both of Japan

[73] Assignee: Olympus Optical Co., Ltd., Tokyo, Japan

[21] Appl. No.: 199,638

[22] Filed: Oct. 22, 1980

[30] Foreign Application Priority Data

Oct. 26, 1979 [JP] Japan .................................. 54-137739

[51] Int. Cl.³ ............................................ G01N 27/28
[52] U.S. Cl. ............................ 204/299 R; 204/180 G; 204/180 S; 23/230 B
[58] Field of Search ............ 204/299 R, 180 G, 180 S; 23/230 B; 222/143

[56] References Cited

U.S. PATENT DOCUMENTS

| 3,238,115 | 3/1966 | Pedersen | 204/180 R |
| 3,499,360 | 3/1970 | Davis | 204/180 G X |
| 3,616,387 | 10/1971 | Siebert | 204/180 G |
| 3,964,992 | 6/1976 | Krotz | 204/299 R |
| 4,059,501 | 11/1977 | Strickler | 204/299 R |
| 4,094,759 | 6/1978 | Ruhenstroth-Bauer et al. | 204/180 G |
| 4,124,470 | 11/1978 | Dahms | 204/180 G X |
| 4,130,471 | 12/1978 | Frosch et al. | 204/180 G |

FOREIGN PATENT DOCUMENTS 54-158692 11/1979 Japan .

Primary Examiner—Arthur C. Prescott
Attorney, Agent, or Firm—Cushman, Darby & Cushman

[57] ABSTRACT

A sample tray feeding apparatus capable of preventing water contents from being evaporated from samples even after sample application comprising a sample tray accommodating container capable of accommodating plural number of sample trays in piled up conditions and having a front opening and a rear opening at the lower end thereof, a shifting mechanism for displacing the lowermost sample tray and a plural number of sample tray covers arranged in a row in the vicinity of the rear opening of said sample tray accommodating container, said sample tray feeding apparatus being adapted in such a manner that said shifting mechanism functions to displace the sample trays to a sample adhering position through the front opening for adhering sample to a blade and then to the position under the sample tray covers through the rear opening.

5 Claims, 6 Drawing Figures

SAMPLE TRAY FEEDING APPARATUS

BACKGROUND OF THE INVENTION (a) Field of the Invention

The present invention relates to a sample tray feeding apparatus for the electrophoretic systems, and more specifically to a sample tray feeding apparatus so adapted as to permit recovering excessive samples remaining after analyses.

(b) Description of the Prior Art

Automatic electrophoretic systems use samples trays having such a construction, for example, as shown in FIG. 1. Speaking concretely, the sample tray 1 has plural cavities for containing samples 2. Such sample trays are accommodated in a sample tray accommodating container in a condition where they are filled with samples, and fed consecutively by a sample tray feeding apparatus for applying samples onto a carrier and other purposes. There have conventionally been known sample tray feeding apparatus having such a construction, for example, as shown in FIG. 2. Speaking concretely, the sample tray feeding apparatus shown in FIG. 2 consists of a sample tray accommodating container 3 having inside dimensions nearly equal to the outside dimensions of the sample tray 1 and so designed as to accommodate multiple sample trays 1 in piled-up condition and a piston type sample tray feeding mechanism 6 both of which are mounted on a stand 4, in addition to a sample tray receiving container 7 located beside the stand 4 and used for accommodating sample trays having been used for sample application. Piled up in this sample tray accommodating container are sample trays 1 which have been inserted through an upper opening 3a, and mounted on the sample tray located at the uppermost position is a sample tray protective cover 5.

Therefore, the sample tray 1 located at the uppermost position is covered with the protective cover 5, whereas the other sample trays are covered with the sample trays mounted thereon respectively so as to prevent evaporation of water contents from the samples contained in the sample trays. Further, formed in the lower end of the sample tray accommodating container is a front opening 3b having a size just permitting a single sample tray to pass therethrough at a time. By operating a pushing rod 6a of the sample tray shifting mechanism in the direction indicated by the arrow, the sample tray located at the lowermost position is pushed out of the container 3 through the opening 3b and displaced to the position represented by the reference symbol A. When the pushing rod 6a of the sample tray shifting mechanism 6 is returned to its initial position, the rest sample trays are allowed to go down until the second lowest sample tray is located at the lowermost position. On the other hand, a sample is allowed to adhere to a blade 9 of a sample applicator 8 when it is lowered down. The blade 9 is then lifted up, shifted to the position designated by the reference symbol B and then lowered down once again to apply the sample onto a carrier 10. Successively, when the second sample tray located now at the lowermost position is shifted to the position A by operating the sample tray shifting mechanism 6, the first sample tray located at the position A is pushed by the second sample tray and dropped down into the receiving container 7. The sample tray feeding apparatus repeats the above-mentioned operations consecutively. In this while, evaporation of water content from the samples 2 is prevented since they are kept in sealed condition owing to the protective cover and the sample trays mounted thereover. The sample tray feeding apparatus described above had a drawback that it functions to drop the sample trays 1 having been used for sample application into the receiving container 7 and therefore permitted no reuse of samples even when they are necessary for re-inspections etc. Moreover, the receiving container arranged between the sample adhering position and the sample applying position unavoidably prolonged the distance to be reserved between these positions, thereby requiring a long time to displace the blade 9 between the positions A and B. Accordingly, samples are dried after they are allowed to adhere to the balde until they are applied onto a carrier, thereby resulting in undesirable effects on analytical results.

SUMMARY OF THE INVENTION

A general object of the present invention is to provide a sample tray feeding apparatus comprising a sample tray accommodating container which is capable of accommodating sample trays in piled up condition and has front and rear openings formed at the lower end thereof and having a size permitting said sample trays to pass therethrough, a protective cover mounted on the sample tray located at the uppermost position, sample tray covers arranged in a row at the back of said rear opening of said sample tray accommodating container and a sample tray shifting mechanism for displacing the sample tray located at the lowermost position, said sample tray feeding apparatus being adapted in such a manner that said sample tray shifting mechanism displaces a sample tray through said front opening to a sample adhering position and then through said rear opening to another position under said sample tray cover, whereby evaporation of water contents from the samples are prevented by said sample tray cover even after said sample is applied onto a carrier.

DETAILED DESCRIPTION OF THE PREFERRED EMBODIMENT

Figure 1:
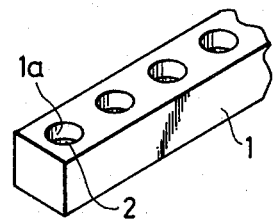
FIG. 1 shows a perspective view illustrating the conventional sample tray.
Figure 2:
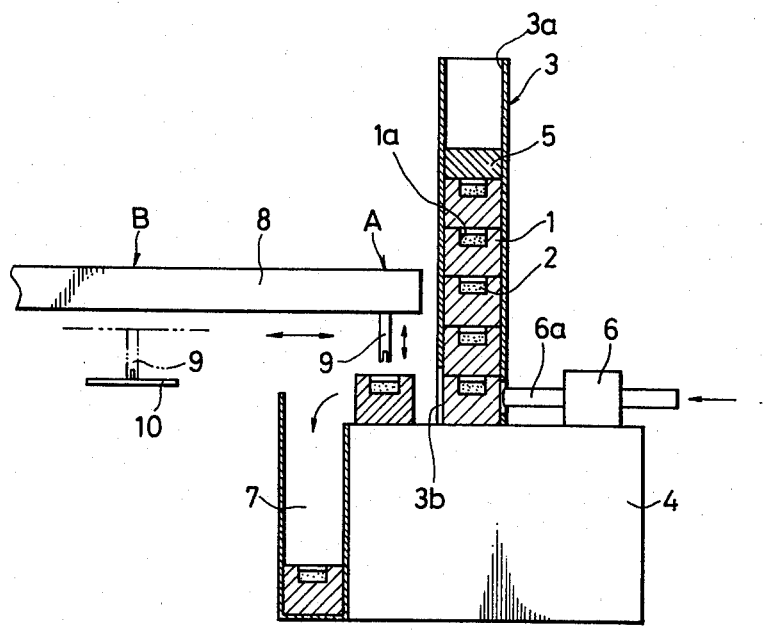
FIG. 2 shows a vertical sectional view illustrating the conventional sample tray feeding apparatus.
Figure 3A:
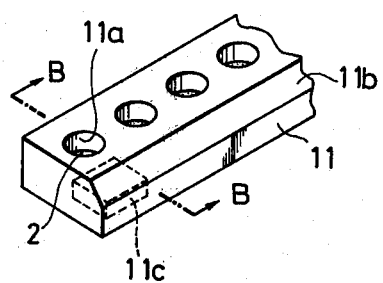
FIG. 3A shows a perspective view of a sample tray to be used with the sample tray feeding apparatus according to the present invention.
Figure 3B:
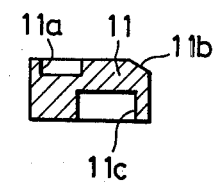
FIG. 3B shows a sectional view taken along the B—B line in FIG. 3A.
Figure 4:
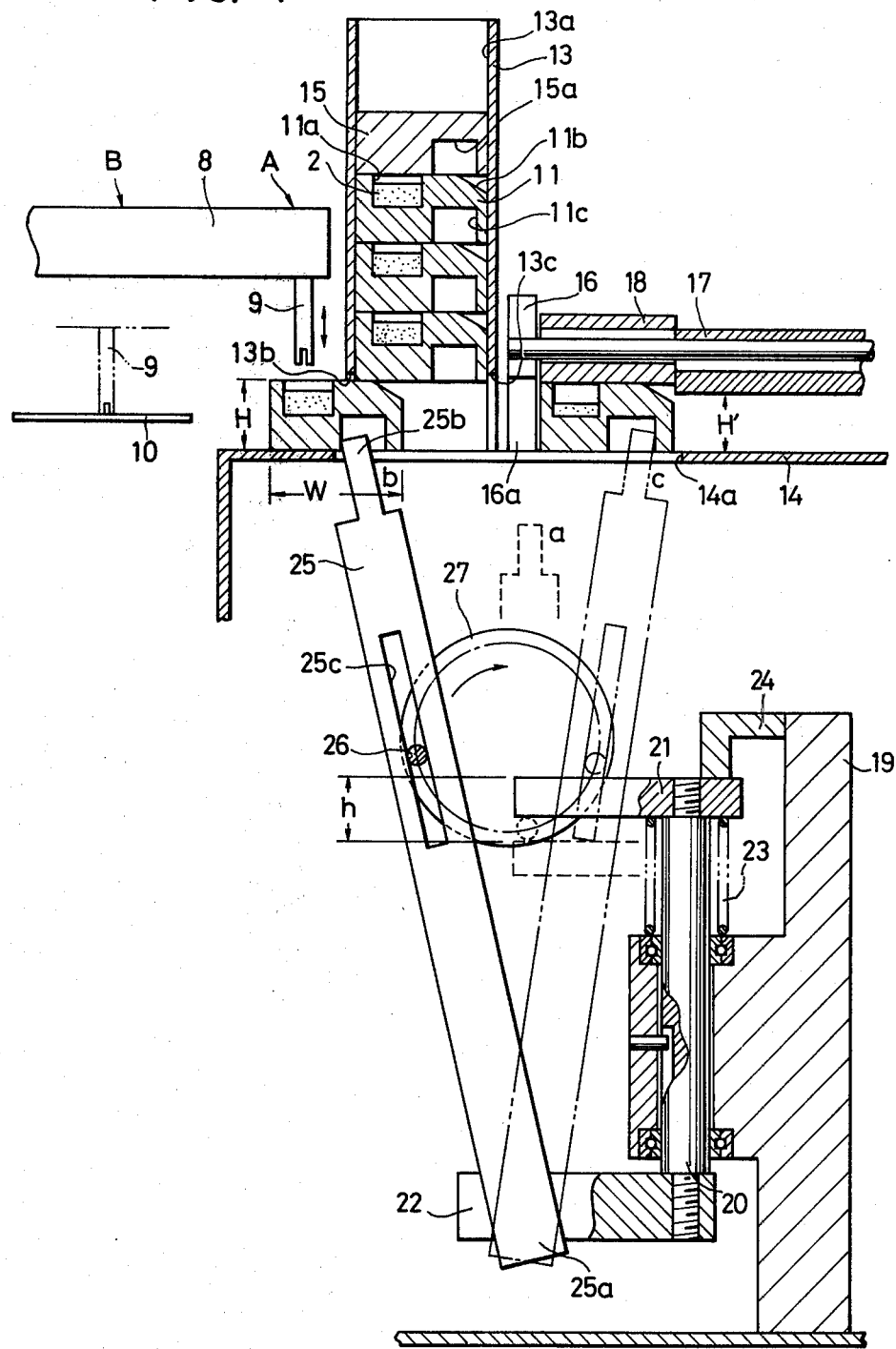
FIG. 4 shows a vertical sectional view illustrating construction of an embodiment of the sample tray feeding apparatus according to the present invention.

Now, an embodiment of the sample tray feeding apparatus according to the present invention will be described with reference to the accompanying drawings. FIG. 3A and FIG. 3B show a sample tray 11 to be used with the sample tray feeding apparatus according to the present invention. This sample tray 11 has plural number of cavities 11a formed on the front side in the top surface thereof, a slant surface 11b formed on the rear side thereof and a pair of right and left engagement holes 11c which are to be engaged with a sample tray shifting lever described later. FIG. 4 shows the sample tray feeding apparatus according to the present invention, wherein the reference numeral 13 represents a sample tray accommodating container having a construction basically the same as that of the conventional sample tray accommodating container shown in FIG. 2 and equipped at the lower end thereof with a rear opening 13c of a size permitting the sample tray 11 to pass therethrough in addition to the openings 13a and 13b. The reference numeral 14 designates a stand having a construction which is basically the same as that of the stand 4 and equipped with a pair of right and left slots 14a which are elongated in the backforth direction so as to permit passing the sample tray shifting lever described later. The reference numeral 15 denotes a sample tray protective cover equipped on the rear side in the bottom thereof with a pair of right and left engagement holes 15a to be engaged with the top end of the sample tray shifting lever described later, and the reference numeral 16 represents a fixed member removably arranged on the stand 14 at the back and in the vicinity of the sample tray accommodating container, and equipped at the lower end thereof with an opening of a size permitting the sample tray 11 to pass therethrough. The reference numeral 17 designates a horizontal support rod which is fixed at the front end thereof to the fixed member 16 and extending backward, and the reference numeral 18 denotes a plural number of sample tray covers which are supported on the horizontal support rod 17 in such a manner as to be vertically movable within a definite range and whose bottoms are kept at a height (height H' as measured from the top surface of the stand 14 to the bottom of the sample tray cover) lower than the top surface of the sample tray 11 mounted on the stand 14 (thickness H of the sample tray 11). The reference numeral 19 represents a support member placed on the bottom surface of the stand 14, the reference numeral 20 designates a vertical support shaft which is attached to the support member 19 so as to be movable in the vertical direction, the reference numeral 21 denotes an upper lever fixed to the upper end of the vertical support shaft 20, the reference numeral 22 represents a lower level fixed to the lower end of the vertical support shaft, and the reference numeral 23 designates a spring which is interposed between the upper lever 21 and support member 19 and functions to push upward the vertical support shaft 20, the upper lever 21 and lower lever 22. The reference numeral 24 denotes a stopper which functions to limit to a certain height the upward movement of the entire assembly of the vertical support shaft 20, the upper lever 21 and lower lever 22. The reference numeral 25 represents a sample tray shifting lever whose lower end is hinged to the lower lever 22 and which can swing as a whole in a vertical plane. The sample tray shifting lever has an upper end 25b which passes through the slots 14a formed in the stand 14 and engaged with the engagement holes 11c formed in the sample tray 11. In addition, a longitudinally elongated slot 25c is formed at the middle portion of the sample tray shifting lever 25. The reference numeral 26 designates a driving pin which is fixed to the outer circumference of a disk 27 rotated by a motor (not shown) and whose tip is slidably fitted into the slot 25c. When the disk 27 is rotated clockwise in FIG. 4 to displace the driving pin 26, the upper end 25a of the sample tray shifting lever 25 is vertically moved and swung consecutively from the reset position a (position traced in the dashed lines in FIG. 4) to the forward dead position b (position traced in the solid lines in FIG. 4) and further to the backward dead position c (position traced in the chain lines in FIG. 4). When the tip 25a of the sample tray shifting lever 25 is set at the position a during the movement described above, the driving pin 26 functions to depress the upper lever 21 downward from its upper limit height by a stroke h against the elastic force of the spring 23 and, accordingly, the sample tray shifting lever 25 is also lowered downward from its upper limit height by the stroke h. At the forward dead position b, the driving pin 26 disengages from the upper lever 21, thereby raising the sample tray shifting lever 25 under the elastic force of the spring 23 by the stroke h up to the height limited by the stopper 24. Further, at the backward dead position c at which the driving pin 26 has not depressed the upper lever 21 yet, the sample tray shifting lever 25 remains at the upper limit height. Moreover, the distance to displace the sample tray 11 forward from the front opening 13b by moving the upper end 25b of the sample tray shifting lever 25 from the reset position a to the forward dead position b is shorter than the longitudinal width W of the sample tray 11 but is so selected as to be sufficient to expose the cavity 11a outside the sample tray accommodating container 13. In addition, the distance to displace the sample tray 11 backward from the rear opening 13c by moving the upper end 25b of the sample tray shifting lever 25 from the forward dead position b to the backward dead position c is so selected as to be longer than the longitudinal width W of the sample tray 11.

Now, functions of the sample tray feeding apparatus according to the present invention will be described below. In the first place, a plural number of sample trays 11 are inserted consecutively into the sample tray accommodating container 13 through the upper opening 13a thereof. Since the inside dimensions of the sample tray accommodating container 13 are nearly equal to the outside dimensions of the sample trays 11, they are dropped always in the horizontal positions and piled up precisely in the sample tray accommodating container 13. Then, the sample tray protective cover 15 is inserted through the upper opening 13a to be mounted on the uppermost sample tray. At this stage, the upper end 25b of the sample tray shifting lever 25 is kept stationary at the reset position a. When the disk 27 is rotated at the next stage, the driving pin 26 disengages from the upper lever 21, whereby upper end 25b of the sample tray shifting lever 25 rises to engage with the engagement holes 11c formed in the lower most sample tray 11. When the upper end 25b of the lever 25 is moved to the forward dead position b subsequently, the lowermost sample tray passes through the front opening 13b of the sample tray accommodating container 13 and is moved until the cavity 11a reaches the sample adhering position A. At this position, the sample applicator 8 is lowered down to allow the sample 2 to adhere to the blade 9, and is moved to the sample applying position B for applying the sample onto the carrier 10. Since the distance of the forward displacement of the sample tray is shorter than the longitudinal width of the sample tray as already described above, the rear end of the sample tray remains inside the sample tray accommodating container 13 as shown in FIG. 4. Therefore, the second and later sample trays are not allowed to go down but remain at their initial height respectively.

As the upper end 25b of the sample tray shifting lever 25 is moved to the backward dead position at the next stage, the lowermost sample tray 11 which has been used for sample application is moved backward while passing through the rear opening 13c of the sample tray accommodating container 13 and the opening 16a formed in the fixed member 16. At this stage, the sample tray 11 is moved while lifting up the sample tray cover 18 with the slanted surface 11b thereof and is stopped at a position at which the cover 18 is just mounted on the sample tray 11. During this backward movement of the sample tray 11, the rest sample trays 11 and the protective cover 15 allowed to go down by their own weights for a distance equal to the height of a single sample tray so that the second sample tray is located at the lowermost position. Successively, the upper end 25b of the sample tray shifting lever 25 starts moving forward and, simultaneously, the driving pin 26 begins to depress the upper lever 21 downward for lowering the upper end 25b of the lever 25. Since the lowering speed of the upper end 25b of the lever 25 is higher than its forward shifting speed, the upper end 25b of the lever 25 disengages from the engagement holes 11b and returns to the reset position a without moving forward the sample tray 11 having been used for sample application.

The operations described above are repeated until all the samples 2 contained in all the sample trays set in the sample tray accommodating container 13 have been applied onto the carrier and all the sample trays have been sent under the sample tray covers 18. After completing analyses of the samples, the sample trays 11 having been used for sample application can be recovered by dismounting the fixed member 16 which is used for supporting the sample tray covers 18 together with the horizontal support rod 17 from the stand 14.

While the above-mentioned operations are being performed, the sample trays 11 are kept in sealed condition by the protective cover and the sample trays mounted immediately thereon, thereby preventing water contents of the samples from being evaporated. Further, even after the samples have been applied onto the carrier, the individual sample trays 11 are kept in sealed condition by the sample tray cover 18, thereby preventing water contents of the residual samples 2 from being evaporated. It is therefore possible to reuse the samples remaining in the sample trays after the sample application for the purpose of re-inspections, etc.

Furthermore, the sample tray feeding apparatus according to the present invention permits shortening the distance to be reserved between the sample adhering position A and the sample applying position B since it uses no member between these two position. As a result, the time required for shifting the blade 9 is shortened to prevent the samples 2 from being dried during the period of time required from sample adhering to the blade to the sample application onto the carrier 10.

Moreover, during the back-forth displacement of the lowermost sample tray, the other sample trays are supported by the lowermost sample tray and not allowed to go down. The sample tray feeding apparatus according to the present invention requires no particular mechanisms for holding the second and later sample trays during displacement of the lowermost sample tray and dropping the second and later sample trays after completing displacement of the lowermost sample tray.

Figure 5:
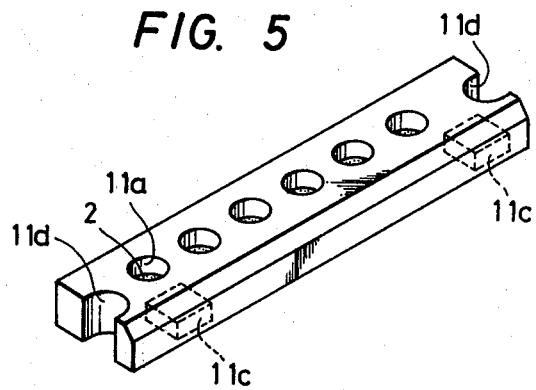
FIG. 5 shows a perspective view of another example of a sample tray to be used with the sample tray feeding apparatus according to the present invention.

FIG. 5 shows another example of sample tray to be used with the sample tray feeding apparatus according to the present invention. The sample tray shown in this drawing has the same construction as that of the sample tray illustrated in FIG. 3A, except the U-shaped cavities 11d which are formed at the right and left ends thereof.

When this sample tray is used with the sample tray feeding apparatus according to the present invention, vertical guides into which said cavities 11d are to be fitted are formed in the right and left inside walls of the sample tray accommodating container. In this case, since the sample trays are dropped while being kept in their horizontal positions along these vertical guides, it is sufficient to design the sample tray accommodating container so as to have inside dimensions larger than those of the sample tray, thereby eliminating the necessity to design the inside dimensions of the sample tray accommodating container so as to be equal to the outside dimensions of the sample tray.

As is understood from the foregoing descriptions, the sample tray feeding apparatus according to the present invention is capable of preventing water contents of samples contained in sample trays from being evaporated not only before sample application but also after sample application. Further, since the sample tray feeding apparatus according to the present invention uses no member arranged between the sample adhering position and the sample applying position, it makes it possible to shorten the distance between the sample adhering position and the sample applying position or the time required after the sample adhering to the blade till the sample application onto the carrier, thereby preventing samples from being dried before sample application and undesirable influence on analytical results due to concentration of the samples. Furthermore, the sample tray feeding apparatus according to the present invention prevents water contents of samples contained in the sample trays from being evaporated even after the sample application, thereby making it possible to reuse residual samples for re-inspections and other purposes. Moreover, the sample tray feeding apparatus according to the present invention has a simple construction since it requires no particular mechanism for preventing the second and later sample trays from being dropped during displacement of the lowermost sample tray.

We claim:

1. A sample tray feeding apparatus comprising sample trays each having plural number of cavities to be filled with samples, a sample tray accommodating container used for accommodating said sample trays in piled up condition and having at the lower end thereof a front opening and a rear opening each being of a size permitting to pass a single sample tray therethrough at a time, a sample tray protective cover to be mounted on the uppermost sample tray, a plural number of sample tray covers arranged movably in the vertical direction in a row at the back of the rear opening of said sample tray accommodating container and a shifting mechanism for displacing the lowermost sample tray, said sample tray feeding apparatus being adapted in such a manner that said shifting mechanism functions to displace the lowermost sample tray to a sample adhering position through the front opening of said sample tray accommodating container and then to the position under said sample tray cover through said rear opening after the sample application.

2. A sample tray feeding apparatus according to claim 1 wherein each of said sample trays has a slanted surface formed on the top rear thereof and serving to push up said sample tray cover so as to position said sample tray under said sample tray cover when said sample tray is shifted through the rear opening of said sample tray accommodating container.

3. A sample tray feeding apparatus according to claim 1 wherein said shifting mechanism consists of a lever which can swing and move vertically, and each of said sample trays has engagement holes formed in the rear bottom thereof to be engaged with the upper end of said lever.

4. A sample tray feeding apparatus according to claim 3 wherein said protective cover has engagement holes formed in the rear bottom thereof to be engaged with the upper end of said lever.

5. A sample tray feeding apparatus according to claim 1 comprising additionally a fixed member arranged in the vicinity of the rear opening of said sample tray accommodating container and having an opening permitting to pass a sample tray at a time, and a horizontal support rod having one end fixed to said fixed member and extending backward so as to support loosely said sample tray covers.

* * * * *